US008022201B2

(12) United States Patent
Roos et al.

(10) Patent No.: US 8,022,201 B2
(45) Date of Patent: Sep. 20, 2011

(54) PROCESS FOR PREPARING AMIDES FROM KETOXIMES

(75) Inventors: Martin Roos, Haltern am See (DE); Stephanie Schauhoff, Langen (DE); Martin Trageser, Gelnhausen-Hoechst (DE); Hans-Peter Krimmer, Kirchweidach (DE)

(73) Assignee: Evonik Degussa GmbH, Essen (DE)

( * ) Notice: Subject to any disclaimer, the term of this patent is extended or adjusted under 35 U.S.C. 154(b) by 257 days.

(21) Appl. No.: 12/296,498

(22) PCT Filed: Apr. 3, 2007

(86) PCT No.: PCT/EP2007/053239
§ 371 (c)(1), (2), (4) Date: Oct. 8, 2008

(87) PCT Pub. No.: WO2007/125002
PCT Pub. Date: Nov. 8, 2007

(65) Prior Publication Data
US 2009/0306367 A1  Dec. 10, 2009

(30) Foreign Application Priority Data
Apr. 28, 2006  (DE) .................. 10 2006 019 769

(51) Int. Cl.
*C07D 201/04* (2006.01)
(52) U.S. Cl. ........................ 540/464; 540/535
(58) Field of Classification Search ............ 540/464, 540/535
See application file for complete search history.

(56) References Cited

U.S. PATENT DOCUMENTS 6,639,108 B2   10/2003  Schiffer et al.
6,828,449 B2   12/2004  Herwig et al.
6,861,540 B2   3/2005   Herwig et al.
6,926,809 B2   8/2005   Puschner et al.
6,927,308 B2   8/2005   Leininger et al.
7,084,300 B2   8/2006   Herwig et al.
7,253,329 B2   8/2007   Herwig et al.
7,495,129 B2   2/2009   Balduf et al.
2007/0004903 A1  1/2007  Hoff et al.
2007/0265184 A1  11/2007  Herwig et al.
2008/0249300 A1  10/2008  Herwig et al.

FOREIGN PATENT DOCUMENTS

DE   103 44 469       4/2005
JP        46023740  *  7/1971

OTHER PUBLICATIONS

Furuya, Y. et al.,"Cyanuric Chloride as a Mild and Active Beckmann Rearrangement Catalyst", J. Am. Chem. Soc., vol. 127, No. 32, pp. 11240-11241, 2005. XP-002441494.
Chapman, A.,"Studies of the Beckmann Change. Part II. The Kinetics of the Spontaneous Rearrangement and Solvent Effects", Journal of the Chemical Society, pp. 1550-1555, 1934. XP008080723.
Venkatswamy, G. et al.,"Action of Cyanuric Chloride on Aldoximes & Ketoximes", Indian J. Chem. Section B: Organic and Medicinal Chemistry, vol. 15B, pp. 740-741, 1977. XP008080771.
U.S. Appl. No. 12/922,807, filed Sep. 15, 2010, Hannen, et al.
U.S. Appl. No. 12/865,018, filed Jul. 28, 2010, Hannen, et al.

* cited by examiner

*Primary Examiner* — Bruck Kifle
(74) *Attorney, Agent, or Firm* — Oblon, Spivak, McClelland, Maier & Neustadt, L.L.P.

(57) ABSTRACT

The present invention is directed to a process for preparing amides. In particular, the process is directed to a process performable on the industrial scale, in which a ketoxime can be converted to a cyclic or acyclic amide by means of a Beckmann rearrangement using 2,4,6-trichloro-1,3,5-triazine as a catalyst in a nonpolar organic solvent.

16 Claims, No Drawings

PROCESS FOR PREPARING AMIDES FROM KETOXIMES

The present invention is directed to a process for preparing amides. In particular, the process is directed to a process performable on the industrial scale, in which a ketoxime can be converted to a cyclic or acyclic amide by means of a Beckmann rearrangement.

The Beckmann rearrangement is used to prepare amides starting from ketoximes. Of particular significance on the industrial scale are the preparation of caprolactam to prepare nylon-6 and the preparation of lauryllactam for nylon-12 (Beyer Walter, Lehrbuch der organischen Chemie [Textbook of Organic Chemistry], 22nd Edition, Stuttgart 1991, p. 546).

The reaction is typically performed in strongly acidic media at high temperatures, which leads to high by-product contents and, associated with this, complicated purification and reduced yields, and is associated with high energy costs.

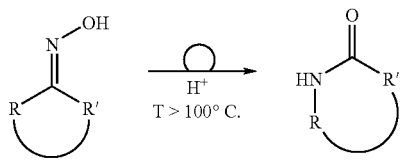

The literature describes a further variant of the Beckmann rearrangement using cyanuric chloride as a catalyst under mild reaction conditions (JACS 2005, 127, 11240). By this method, acyclic and cyclic amides can be synthesized in good yields from the corresponding ketoximes with addition of catalytic amounts of cyanuric chloride in the presence of catalytic amounts of $ZnCl_2$.

A disadvantage of the method is that, according to literature data, good yields are obtained only in polar solvents such as acetonitrile and nitromethane, while only a low conversion is achieved in nonpolar solvents and, for example, the 9-membered ring lactam is obtained only in very low yield.

For industrial scale use, however, a reaction in nonpolar solvents is required, since the oxime precursor is obtained in nonpolar solvents and complicated intermediate steps would thus be required to change the solvent and additional solvent costs would arise if the literature process using cyanuric chloride were to be used. Such a process would have a clear disadvantage in industrial scale use.

It is therefore an object of the invention to specify a further process for preparing amides by means of Beckmann rearrangement, which, in spite of the use of cyanuric chloride as a catalyst, can dispense with the use of such polar solvents. Specifically on the industrial scale, the process according to the invention should be superior to the prior art process from the ecological and also economic point of view. In particular, the current process shall be capable of delivering a not significantly poorer conversion of ketoxime in a less polar solvent or solvent mixture with a not significantly greater use amount of cyanuric chloride.

It has now been found that, surprisingly, in a process for preparing amides from the corresponding ketoximes by heating the ketoxime in the presence of cyanuric chloride, the amides can be obtained in excellent yields even when the reaction is performed in a nonpolar organic solvent having a log P value of 2-14, and the solvent must not consist exclusively of toluene when the use amount of cyanuric chloride is $\leq 5$ mol %.

This was by no means to be expected against the background of the known prior art. In particular, it can be considered surprising that merely the fact of a negligibly low increase in the use amount of cyanuric chloride in nonpolar solvents is apparently sufficient to extend the teaching, propagated by the prior art, of the use of polar and nucleophilic solvents in this reaction also to the successful use of nonpolar solvents.

The substrates used in the inventive reaction may be either cyclic or acyclic ketoximes. The amount of cyanuric chloride can be adjusted by the person skilled in the art according to the synthesis problem present in each case. Factors to be considered for the balancing of the use amount include the reaction rate, space-time yield and/or by-product formation.

The reaction is preferably performed in the presence of an amount of cyanuric chloride based on the ketoxime of 0.5-30 mol %.

It has been found that the amount of cyanuric chloride added can vary in relation to the synthesis problem of the conversion of open-chain or cyclic ketoximes. For cyclic ketoximes, a use amount of cyanuric chloride based on the amount of ketoxime of 0.5-30 mol % may preferably be taken. More preferred is the use of an amount of 0.5-20 mol %, more preferably of 1-15 mol % and especially preferably of 1.5-13 mol % of cyanuric chloride.

For acyclic ketoximes, a use amount of cyanuric chloride based on the amount of ketoxime of 0.5-30 mol % can preferably be taken. More preferred is the use of an amount of 0.5-20 mol %, more preferably of 1-10 mol % and especially preferably of 2-6 mol % of cyanuric chloride.

The selection of the nonpolar solvent is left to the person skilled in the art in the inventive context. The polarity of solvents can be defined by the so-called logP value. This is defined as the decadic logarithm of the partition coefficient P of a substance in octanol-water (Lit.: J. Phys. Chem. Ref. Data, Vol. 18, No. 3, 1989). In a preferred embodiment, the logP value of the solvent is 2-10, more preferably 2.5-8 and very preferably 3-7.

Specifically, useful solvents in the reaction have been found to be solvents or solvent mixtures from the group consisting of cyclodecane, cyclooctane, cycloheptane, cyclohexane, cyclopentane, n-nonane, n-octane, n-heptane, n-hexane, n-pentane, isooctane, hydrocumene, toluene, benzene, and the like. Very particular preference is given to the use of cyclododecane, cyclooctane and hydrocumene or mixtures thereof in this context.

Even though the use of a cocatalyst has not been found to be necessary in the present experiments, it might be favourable for certain synthesis problems to add one to the reaction. Useful cocatalysts are in particular Lewis acids or Brönsted acids. Such acids can be selected from the group consisting of $ZnCl_2$, $FeCl_3$, $CoCl_2$, $PbCl_3$, $SnCl_3$, $TiCl_2$, $ZrCl_2$, or HCl, $H_2SO_4$, $H_3PO_4$, $HNO_3$, p-toluenesulphonic acid, methylsulphonic acid, and the like. Very particular preference is given to the use of weak Lewis acids such as zinc chloride, iron chloride, cobalt chloride, or Brönsted acids such as HCl, $H_2SO_4$, p-toluenesulphonic acid.

The use amount of the cocatalyst can be selected by the person skilled in the art according to his or her knowledge. In the present case, possible use amounts are 0.5-20 mol % based on the ketoxime, preferably 0.5-10 mol % and most preferably 1-4 mol %.

The reaction is preferably performed in such a way that the substrate is initially charged in the nonpolar solvent and the cyanuric chloride is added to the mixture. Subsequently, the reaction mixture is heated, for which a temperature of 50-250° C. is established. The temperature of the reaction is preferably 80-120° C., most preferably 100-115° C.

On completion of the reaction, which, at the temperatures specified above, has ended generally within at least 3 h, preferably 2 h, more preferably <1 h and very particularly <15 min, the mixture can be worked up as determined by the person skilled in the art. For this purpose, the solution is preferably cooled, and the lactam is allowed to crystallize out and filtered off; the product can if appropriate be purified further by recrystallization.

It is advantageous to use 5 mol % of cyanuric chloride for the reaction of acyclic ketoximes with a yield of >85% of amide. In contrast to the literature data, this is the case both for polar and for nonpolar solvents. Lower concentrations usually lead to lower conversions; although higher concentrations lead to a 100% conversion of the oxime, the risk of by-product formation can increase.

Cyclic ketoximes which are used in the reaction preferably have a ring size of 6-12, more preferably 7-12 and more preferably 7-9 or more preferably 10-12.

Cyclic ketoximes having ring sizes of 10-12 can be converted preferably in hydrocumene or cyclooctane, in which case 100% conversion and yields of >90% can be obtained with 2-3 mol % of cyanuric chloride. In polar solvents such as acetonitrile, merely a cyanuric chloride concentration of 1 mol % is sufficient for full conversion. Unconverted ketone from the precursor does not disrupt the reaction.

For the conversion of smaller rings (ring sizes 6-9, preferably 7-9), a cyanuric chloride concentration of 3-13 mol % is advantageously used. This likewise allows conversions of >85% to be achieved within appropriate time windows.

The reaction can proceed batchwise in a stirred tank or continuous in a tubular reactor, stirred tank or a stirred tank battery.

Interestingly, the present invention shows that, contrary to the teaching which can be taken from the cited prior art, it is entirely possible to achieve the catalytic Beckmann rearrangement with cyanuric chloride even in nonpolar solvents with very high yields. Specifically the example in the JACS Publication in Table 1, entry 11, would if anything have deterred the person skilled in the art from the use of nonpolar solvents in the present reaction, since toluene here as a solvent affords just an 8% yield. However, it has been shown in the present case that a slight increase in the cyanuric chloride concentration surprisingly drastically increases the yield of product, which is why the preparation variants described here can be used exceptionally preferably specifically on the industrial scale. However, it is thus not rendered obvious in any way by the present prior art. It should be emphasized very particularly that the 9-membered ring lactam too can be prepared in economically advantageous yields by the process according to the invention.

In addition, the use of nonpolar solvents is particularly advantageous for reasons of process economics against the background that the precursors used here are likewise prepared in nonpolar solvents, since a solvent change from nonpolar to polar solvents in the preparation of amides and lactams can thus be avoided.

The oximes to be used for the present inventive reaction can be obtained by processes known to those skilled in the art (Organikum, VEB Deutscher Verlag der Wissenschaften, Berlin 1986, 16th Edition, p. 394ff.).

EXAMPLES

The reactions were all performed with in each case 2 mmol of the particular oxime in 4 ml of solvent with addition of different amounts of cyanuric chloride as a catalyst. All solvents were used in analytical grade. The reaction was monitored by means of GC, and conversion and yield were determined from the area percentages. The yields are each based on the amount of oxime used.

Ex. 1

Reaction of acetophenone oxime in ACN with 1 mol % of CYC for 60 min under reflux. Conversion 61%, lactam yield 61%.

Ex. 2

Reaction of acetophenone oxime in ACN with 5 mol % of CYC for 60 min under reflux. Conversion 99%, lactam yield 99%.

Ex. 3

Reaction of acetophenone oxime in toluene with 10 mol % of CYC for 60 min under reflux. Conversion 98%, lactam yield 60%.

Ex. 4

Reaction of acetophenone oxime in cyclooctane with 1 mol % of CYC for 60 min at 113° C. Conversion 5%, lactam yield 5%.

Ex. 5

Reaction of acetophenone oxime in cyclooctane with mol % of CYC for 60 min at 113° C. Conversion 99%, lactam yield 90%.

Ex. 6

Reaction of acetophenone oxime in cyclooctane with mol % of CYC for 60 min at 113° C. Conversion 99%, lactam yield 60%.

Ex. 7

Reaction of CDON in ACN with 1.1 mol % of CYC for 60 min under reflux. Conversion 100%, lactam yield 100%.

Ex. 8

Reaction of CDON in ACN with 1.6 mol % of CYC for 60 min under reflux. Conversion 100%, lactam yield 100%.

Ex. 9

Reaction of CDON in ACN with 2.2 mol % of CYC for 120 min under reflux. Conversion 100%, lactam yield 100%.

Ex. 10

Reaction of CDON in toluene with 1.6 mol % of CYC for 60 min under reflux. Conversion 18%, lactam yield 18%.

Ex. 11

Reaction of CDON in toluene with 4.3 mol % of CYC for 60 min under reflux. Conversion 98%, lactam yield 98%.

Ex. 12

Reaction of CDON in hydrocumene with 0.7 mol % of CYC for 60 min at 113° C. Conversion 4%, lactam yield 4%.

Ex. 13

Reaction of CDON in hydrocumene with 1.7 mol % of CYC for 60 min at 113° C. Conversion 27%, lactam yield 27%.

Ex. 14

Reaction of CDON in hydrocumene with 1.9 mol % of CYC for 60 min at 113° C. Conversion 97%, lactam yield 97%.

Ex. 15

Reaction of CDON in hydrocumene with 2.1 mol % of CYC for 60 min at 113° C. Conversion 100%, lactam yield 100%.

Ex. 16

Reaction of CDON in hydrocumene with 2.6 mol % of CYC for 10 min at 113° C. Conversion 100%, lactam yield 100%.

Ex. 17

Reaction of CDON in hydrocumene with 2.1 mol % of CYC for 15 min at 113° C. and addition of 2.5% of cyclododecane. Conversion 100%, lactam yield 100%.

Ex. 18

Reaction of CDON in cyclooctane with 1.6 mol % of CYC for 150 min at 113° C. Conversion 28%, lactam yield 28%.

Ex. 19

Reaction of CDON in cyclooctane with 2.7 mol % of CYC for 20 min at 113° C. Conversion 100%, lactam yield 100%.

Ex. 20

Reaction of CDON in cyclododecane with 2.1 mol % of CYC for 30 min at 113° C. Conversion 100%, lactam yield 100%.

Ex. 21

Reaction of CDON in a mixture of hydrocumene and cyclooctane in a volume ratio of 1:1 with 2.1 mol % of CYC for 30 min at 113° C. Conversion 100%, lactam yield 100%.

Ex. 22

Reaction of CDON in a mixture of hydrocumene and cyclododecane in a volume ratio of 1:1 with 2.1 mol % of CYC for 30 min at 113° C. Conversion 100%, lactam yield 100%.

Ex. 23

Reaction of CDON in a mixture of 20% by weight of cyclodecane and 80% by weight of cyclooctane with 2.1 mol % of CYC for 30 min at 113° C. Conversion 100%, lactam yield 100%.

Ex. 24

Reaction of CDON in n-octane with 2.1 mol % of CYC for 60 min at 113° C. Conversion 100%, lactam yield 100%.

Ex. 25

Reaction of CDON in cyclooctane with 1.6 mol % of CYC and 1.0 mol % of sulphuric acid for 30 min at 113° C. Conversion 50%, lactam yield 20%.

Ex. 26

Reaction of c-octanone oxime in cyclooctane with 3.1 mol % of CYC for 30 min at 113° C. Conversion 10%, lactam yield 10%.

Ex. 27

Reaction of c-octanone oxime in cyclooctane with 12.5 mol % of CYC for 30 min at 113° C. Conversion 95%, lactam yield 95%.

Ex. 28

Reaction of a mixture of c-octanone oxime and CDON (58/42 mol %) in cyclooctane with 6.3 mol % of CYC (based on the sum of oximes) for 30 min at 113° C. $C_8$-oxime conversion 100%, $C_{12}$-oxime conversion 100%, C8/C12 lactam yield 100%/100%.

Ex. 29

Reaction of a mixture of c-octanone oxime and CDON (58/42 mol %) in cyclooctane with 12.5 mol % of CYC (based on the sum of oximes) for 30 min at 113° C. $C_8$-oxime conversion 100%, $C_{12}$-oxime conversion 100%, C8/C12 lactam yield 50%/100%.

Ex. 30

Reaction of a mixture of c-hexanone oxime and CDON (63/37 mol %) in hydrocumene with 5.9 mol % of CYC (based on the sum of oximes) for 95 min at 113° C. $C_6$-oxime conversion 90%, $C_{12}$-oxime conversion 90%, C6/C12 lactam yield 20%/50%.

Ex. 31

Reaction of CDON in cyclooctane with 1.6 mol % of CYC and 4.1 mol % of zinc chloride for 60 min at 113° C. Conversion 100%, lactam yield 100%.

Further examples on the industrial scale and with continuous synthesis mode.

Ex. 1.1

100 g of a mixture of 75 g of hydrocumene and 25 g of CDON (0.126 mol, MW 197.3) are admixed with 0.50 g of cyanuric chloride (0.00271 mol, MW 184.4) at 80° C. at a bath temperature of 115° C., and stirred for 30 min. In the course of this, exothermicity up to max. 150° C. sets in after 2-3 min, and has ended after 6-7 min. Subsequently, the mixture is allowed to continue to react at 110-115° C.

GC analysis: 0.4 area % of CDON and 98.6 area % of lauryllactam

Cooled to approx. 10° C. and precipitate filtered off, dried at 70° C. under reduced pressure.

Isolated yield: 23.3 g, lauryllactam=93.2% of theory, MW 197.3

Exp. 1.2

19.8 g of CDON are initially charged in 100 ml of cyclooctane at approx. 80° C. (bath temperature 115° C.), and 0.50 g of cyanuric chloride is added. From 4 min, an exotherm up to 130° C. sets in, which abates again after 8 min. The reaction has ended after 15 min and begins to cool.

GC analysis: 0.06 area % of CDON and 99.6 area % of lauryllactam

Isolated yield: 19.1 g, lauryllactam=96.5% of theory, MW 197.3

Ex. 1.3

A 25% by weight solution of CDON in cyclooctane (temperature 80° C.) [Sol. A] and a 10% by weight solution of cyanuric chloride in cyclooctane (temperature 40° C.) [Sol. B] are metered by means of pumps at a constant flow rate of 10 l/h of Sol. A and 0.6 l/h of Sol. B simultaneously into a reaction coil heated to 115° C., DN 25, length 5.6 m, and a downstream continued reaction zone heated to 100° C., DN 25, length 2.8 m. The resulting reaction solution can then be cooled and sent to product isolation and, if any, purification.

This gives rise to mean residence times of approx. 15 min in the reaction zone and approx. 8 min in the continued reaction, which is sufficient for full conversion.

The gas chromatography analysis of the resulting reaction solution gives 0.08 area % of CDON and 99.2 area % of lauryllactam.

Isolated yield: from 1 l of reaction solution, 238 g of crude, dry lauryllactam were obtained, which corresponds to 95.2% of theory.

Abbreviations:
CYC=cyanuric chloride
ACN=acetonitrile
CDON=cyclododecanone oxime

The invention claimed is:

1. A process for preparing an amide from a corresponding ketoxime, comprising:
   providing a mixture of at least one ketoxime and cyanuric chloride in at least one nonpolar organic solvent; and
   heating the mixture to react the at least one ketoxime,
   wherein the at least one ketoxime is a cyclic ketoxime having a ring size of 6-12, the at least one nonpolar organic solvent has a logP value of 2-14, and the at least one nonpolar organic solvent does not consist exclusively of toluene when an amount of cyanuric chloride in the mixture is $\leqq 5$ mol %.

2. The process according to claim 1,
wherein
the mixture includes 0.5-30 mol % of cyanuric chloride based on an amount of the at least one ketoxime in the mixture.

3. The process according to claim 1,
wherein
the at least one nonpolar organic solvent comprises at least one selected from the group consisting of cyclooctane, hydrocumene and cyclododecane.

4. The process according to claim 1,
wherein
the providing of the mixture comprises providing a mixture of the at least one ketoxime, cyanuric chloride and a cocatalyst.

5. The process according to claim 1,
wherein
the heating comprises heating the mixture to react the at least one ketoxime at a temperature of 50-250° C.

6. The process according to claim 1,
wherein
the providing of the mixture and the heating of the mixture are performed in a continuous process.

7. The process according to claim 1, wherein the at least one ketoxime comprises at least one cyclic ketoxime having a ring size of 6-9.

8. The process according to claim 7, wherein the mixture includes 3-13 mol % of cyanuric chloride based on an amount of the at least one ketoxime in the mixture.

9. The process according to claim 1, wherein the at least one ketoxime comprises at least one cyclic ketoxime having a ring size of 10-12.

10. The process according to claim 9, wherein the at least one nonpolar organic solvent comprises one of cyclooctane and hydrocumene.

11. The process according to claim 9, wherein the mixture includes 3-13 mol % of cyanuric chloride based on an amount of the at least one ketoxime in the mixture.

12. The process according to claim 1, wherein the at least one ketoxime is at least one of cyclododecanone oxime and c-hexanone oxime.

13. The process according to claim 1, wherein the mixture includes 1.5-13 mol % of cyanuric chloride based on an amount of the at least one cyclic ketoxime in the mixture.

14. The process according to claim 1, wherein the mixture includes 2-6 mol % of cyanuric chloride based on an amount of the at least one acyclic ketoxime in the mixture.

15. The process according to claim 1, wherein the heating comprises heating the mixture to react the at least one ketoxime at a temperature of 80-120° C.

16. The process according to claim 1, wherein the heating comprises heating the mixture to react the at least one ketoxime at a temperature of 100-115° C.

* * * * *